US012514722B2

(12) United States Patent
Kallmes et al.

(10) Patent No.: US 12,514,722 B2
(45) Date of Patent: Jan. 6, 2026

(54) CAROTID ARTERY STENTING SYSTEMS AND METHODS

(71) Applicant: Mayo Foundation For Medical Education And Research, Rochester, MN (US)

(72) Inventors: David Kallmes, Rochester, MN (US); Waleed Brinjikji, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1106 days.

(21) Appl. No.: 17/426,921

(22) PCT Filed: Jan. 24, 2020

(86) PCT No.: PCT/US2020/015100
§ 371 (c)(1),
(2) Date: Jul. 29, 2021

(87) PCT Pub. No.: WO2020/159832
PCT Pub. Date: Aug. 6, 2020

(65) Prior Publication Data

US 2022/0096257 A1 Mar. 31, 2022

Related U.S. Application Data

(60) Provisional application No. 62/799,485, filed on Jan. 31, 2019.

(51) Int. Cl.
*A61F 2/95* (2013.01)
*A61F 2/958* (2013.01)
(Continued)

(52) U.S. Cl.
CPC ......... *A61F 2/958* (2013.01); *A61M 25/0032* (2013.01); *A61M 25/1011* (2013.01); *A61M 2025/1052* (2013.01)

(58) Field of Classification Search
CPC .. A61F 2/958; A61F 2/90; A61F 2/06; A61M 25/0032; A61M 25/1011;
(Continued)

(56) References Cited

U.S. PATENT DOCUMENTS

| | | | |
|---|---|---|---|
| 6,595,953 | B1 | 7/2003 | Coppi et al. |
| 2001/0044598 | A1 | 11/2001 | Parodi |

(Continued)

FOREIGN PATENT DOCUMENTS

| | | | |
|---|---|---|---|
| CN | 101396579 | A | 4/2009 |
| WO | 200032266 | A1 | 6/2000 |

(Continued)

OTHER PUBLICATIONS

International Search Report and Written Opinion from PCT App. No. PCT/US20/15100, dated Apr. 23, 2020, 12 pages.

(Continued)

*Primary Examiner* — Jerrah Edwards
*Assistant Examiner* — Kia Xiong White
(74) *Attorney, Agent, or Firm* — Shumaker & Sieffert, P.A.

(57) ABSTRACT

A carotid artery stenting system can include a sheath that is inserted into an artery. The sheath can include a distal portion having a first inflatable balloon, a first distal port configured to enable a stent to exit the sheath, and a second distal port configured to enable a second inflatable balloon to exit the sheath. A distance between the first inflatable balloon and the second inflatable balloon can be customized by moving a catheter distally or proximally inside a lumen of the sheath.

24 Claims, 6 Drawing Sheets

(51) Int. Cl.
*A61M 25/00* (2006.01)
*A61M 25/10* (2013.01)

(58) Field of Classification Search
CPC .. A61M 2025/1052; A61M 2025/0036; A61M 2025/0681; A61M 2025/1045; A61M 2025/1015; A61B 17/12045; A61B 17/12109; A61B 17/12136
See application file for complete search history.

(56) References Cited

U.S. PATENT DOCUMENTS

| | | | | |
|---|---|---|---|---|
| 2002/0016564 | A1 | 2/2002 | Courtney et al. | |
| 2002/0052638 | A1* | 5/2002 | Zadno-Azizi .... | A61B 17/12109 623/1.2 |
| 2002/0169458 | A1 | 11/2002 | Connors | |
| 2009/0254166 | A1 | 10/2009 | Chou et al. | |
| 2009/0299454 | A1* | 12/2009 | Jennings ................. | A61F 2/954 623/1.11 |
| 2014/0024955 | A1* | 1/2014 | Zhadkevich ..... | A61B 17/12031 600/486 |
| 2016/0271315 | A1* | 9/2016 | Chang ................. | A61M 25/104 |
| 2017/0165457 | A1 | 6/2017 | Zhadkevich | |

FOREIGN PATENT DOCUMENTS

| | | | |
|---|---|---|---|
| WO | 200191844 | A1 | 12/2001 |
| WO | 2012109382 | A2 | 8/2012 |
| WO | 2017192999 | A1 | 11/2017 |

OTHER PUBLICATIONS

Extended Search Report from counterpart European Application No. 20749609.2 dated Sep. 15, 2022, 9 pp.

* cited by examiner

CAROTID ARTERY STENTING SYSTEMS AND METHODS

CROSS REFERENCE TO RELATED APPLICATION

The entire contents of the following application are incorporated by reference herein: International Patent Application PCT/US2017/031311; having an international filing date of May 5, 2017 and a priority date of May 6, 2016; and entitled INTERNAL CAROTID ARTERY THROMBECTOMY DEVICES AND METHODS.

BACKGROUND

Field

The invention relates generally to medical devices and methods of use. Embodiments of the invention include devices for performing carotid artery stenting.

Description of Art

Carotid artery stenting is a procedure that opens clogged arteries to restore blood flow to the brain. Oftentimes, such procedures are performed to treat or prevent stroke. Stents and other endovascular tools are sometimes placed in the internal carotid artery ("ICA") or other vasculature using guiding sheaths that do not have balloons. Guiding sheaths can be about ninety centimeters in length. These devices act as a combination of access sheath and guiding catheter. The need for a separate sheath is obviated by the use of these guiding sheaths since they are sufficiently long to provide access to the target vessel. Although guiding sheaths do not provide arterial occlusion, they can be rapidly placed.

There is a continuing need for improved devices and methods for performing mechanical revascularization such as carotid artery stenting in the ICA and other vasculature. In particular, there is a need for such devices and methods that provide enhanced efficacy. Devices and methods of these types that can improve the efficiency of health care delivery would be especially desirable.

Delivering existing carotid artery stenting systems can be very challenging, especially in patients who are older and/or who have complex anatomies. Thus, there is a need for systems and methods that can be more efficiently, effectively and safely delivered to precise locations in complex arterial anatomies.

SUMMARY

In some embodiments, a carotid artery stenting system comprises an elongated sheath configured for insertion into an artery. In some embodiments, an elongated sheath comprises a distal portion having a first inflatable balloon and a first distal port configured to enable a stent to exit the elongated sheath; a proximal portion having a first inflation port and a first access port; a first lumen extending between the first access port and the first distal port; and/or a second lumen extending between the first inflation port and a first interior of the first inflatable balloon.

In some embodiments, a distal portion of the elongated sheath comprises a second distal port. The proximal portion of the elongated sheath can comprise a second access port. The elongated sheath can comprise a third lumen extending between the second distal port and the second access port. A carotid artery stenting system can comprise a first catheter having a second inflatable balloon and a fourth lumen configured to enable inflating the second inflatable balloon.

In some embodiments, at least a portion of the first catheter is located in the third lumen of the elongated sheath such that a distance between the first inflatable balloon and the second inflatable balloon can be customized by moving the portion of the first catheter at least one of distally and proximally inside the third lumen of the elongated sheath.

In some embodiments, a carotid artery stenting system comprises a second catheter configured to deliver the stent. At least a first portion of the second catheter can be located in the first lumen of the elongated sheath. A second portion of the second catheter can be located in the first distal port.

In some embodiments, the second catheter comprises a distal portion having a third inflatable balloon configured to expand the stent in at least one of an internal carotid artery, an external carotid artery, a common carotid artery, any artery in a body of a patient, and any vein in a body of a patient.

In some embodiments, the first inflatable balloon is in a first inflated occlusion state in a common carotid artery, and the second inflatable balloon is in a second inflated occlusion state in an external carotid artery.

In some embodiments, a carotid artery stenting system comprises a second catheter configured to deliver the stent. At least a first portion of the second catheter can be located in the first lumen of the elongated sheath. A second portion of the second catheter can be located in the first distal port. The stent and a distal portion of the second catheter can be located in an internal carotid artery.

In some embodiments, the first inflatable balloon is in a first inflated occlusion state in a common carotid artery, and the second inflatable balloon is in a second inflated occlusion state in an internal carotid artery.

In some embodiments, a carotid artery stenting system comprises a second catheter configured to deliver the stent. At least a first portion of the second catheter can be located in the first lumen of the elongated sheath. A second portion of the second catheter can be located in the first distal port. The stent and a distal portion of the second catheter can be located in an external carotid artery.

In some embodiments, a carotid artery stenting system comprises a second catheter configured to deliver the stent. At least a first portion of the second catheter can be located in the first lumen of the elongated sheath. A first opening of the first distal port can be oriented within plus or minus ten degrees (and/or within plus or minus twenty degrees) of a central axis of a distal end of the elongated sheath such that the first distal port is configured to enable a second portion of the second catheter that is located distally relative to the distal end of the elongated sheath to be axially aligned with the central axis.

Some embodiments comprise a second opening of the second distal port. The second opening can be oriented at an angle of at least twenty degrees (and/or at least forty degrees) relative to the central axis.

In some embodiments, the distal end of the elongated sheath comprises a second opening of the second distal port. The second opening can be oriented at an angle of less than twenty degrees relative to the central axis.

In some embodiments, the first inflatable balloon is located on a first outer perimeter of the elongated sheath. In some embodiments, the second inflatable balloon is not located on a second outer perimeter of the elongated sheath. The second inflatable balloon can be located on a third outer perimeter of the first catheter. The first catheter can comprise a first distal portion having the second inflatable balloon.

The first distal portion of first catheter can be configured to move distally and rotationally independent of the first inflatable balloon.

In some embodiments, the second lumen and the third lumen are located radially outward relative to the first lumen.

In some embodiments, the first lumen comprises a first cross-sectional area that is at least three times larger than a second cross-sectional area of the second lumen.

In some embodiments, the first cross-sectional area is at least two times larger than a third cross-sectional area of the third lumen.

In some embodiments, an inner diameter of the first lumen of the elongated sheath is less than seven French. An inner diameter of the first lumen of the elongated sheath can be less than six French. An inner diameter of the first lumen of the elongated sheath can be less than four French.

In some embodiments, the elongated sheath comprises a working length configured to enable a distal end of the elongated sheath to reach an internal carotid artery of a person from a femoral artery arteriotomy.

Some carotid artery stenting embodiments comprise obtaining an elongated sheath having a distal portion and a proximal portion. The distal portion of the elongated sheath can comprise a first inflatable balloon and a first distal port configured to enable a stent to exit the elongated sheath. The proximal portion of the elongated sheath can comprise a first inflation port and a first access port. The elongated sheath can comprise a first lumen and a second lumen. The first lumen can extend between the first access port and the first distal port such that the first lumen fluidly couples the first access port and the first distal port.

In some embodiments, the second lumen extends between the first inflation port and a first interior of the first inflatable balloon such that the second lumen fluidly couples the first inflation port and the first interior of the first inflatable balloon.

In some embodiments, the distal portion of the elongated sheath comprises a second distal port. The proximal portion of the elongated sheath can comprise a second access port. The elongated sheath can comprise a third lumen extending between the second distal port and the second access port such that the third lumen fluidly couples the second distal port and the second access port.

Some embodiments comprise inserting the elongated sheath into an artery to perform a medical procedure.

Some embodiments comprise moving a first catheter distally (and/or proximally) in the third lumen of the elongated sheath. The first catheter can comprise a second inflatable balloon and a fourth lumen configured to enable inflating the second inflatable balloon.

Some embodiments comprise inflating the first inflatable balloon in a common carotid artery to at least partially occlude the common carotid artery; customizing a distance between the first inflatable balloon in the common carotid artery and the second inflatable balloon in an external carotid artery (or in an internal carotid artery) by moving a portion of the first catheter at least one of distally and proximally inside the third lumen of the elongated sheath; and/or inflating the second inflatable balloon in the external carotid artery (or in the internal carotid artery) to at least partially occlude the external carotid artery (or to at least partially occlude the internal carotid artery).

Some embodiments comprise moving a second catheter having the stent distally in the first lumen of the elongated sheath to move the stent distally through at least a portion of the first lumen and then into an internal carotid artery (or into an external carotid artery).

Some embodiments comprise delivering the stent to a location in the internal carotid artery while a distal end of the elongated sheath is positioned in the common carotid artery; while occluding an area between an outer perimeter of the elongated sheath and an inner wall of the common carotid artery with the first inflatable balloon; while occluding the external carotid artery with the second inflatable balloon of the first catheter; and/or while fluidly coupling the common carotid artery to a pressure source having a lower pressure than a blood pressure of the common carotid artery to apply a suction force to blood in the common carotid artery. The pressure source can comprise a vein.

Some embodiments comprise delivering the stent to a location in the external carotid artery while a distal end of the elongated sheath is positioned in the common carotid artery; while occluding an area between an outer perimeter of the elongated sheath and an inner wall of the common carotid artery with the first inflatable balloon; while occluding the internal carotid artery with the second inflatable balloon of the first catheter; and/or while fluidly coupling the common carotid artery to a pressure source having a lower pressure than a blood pressure of the common carotid artery to apply a suction force to blood in the common carotid artery. The pressure source can comprise a vein.

Some embodiments comprise using a tube to fluidly couple the common carotid artery to the vein. Some embodiments comprise reversing a flow direction of the blood to suction emboli from at least one of the internal carotid artery, the external carotid artery, and the common carotid artery.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout similar embodiments.

DETAILED DESCRIPTION

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

LIST OF REFERENCE NUMBERS

Figure 1:
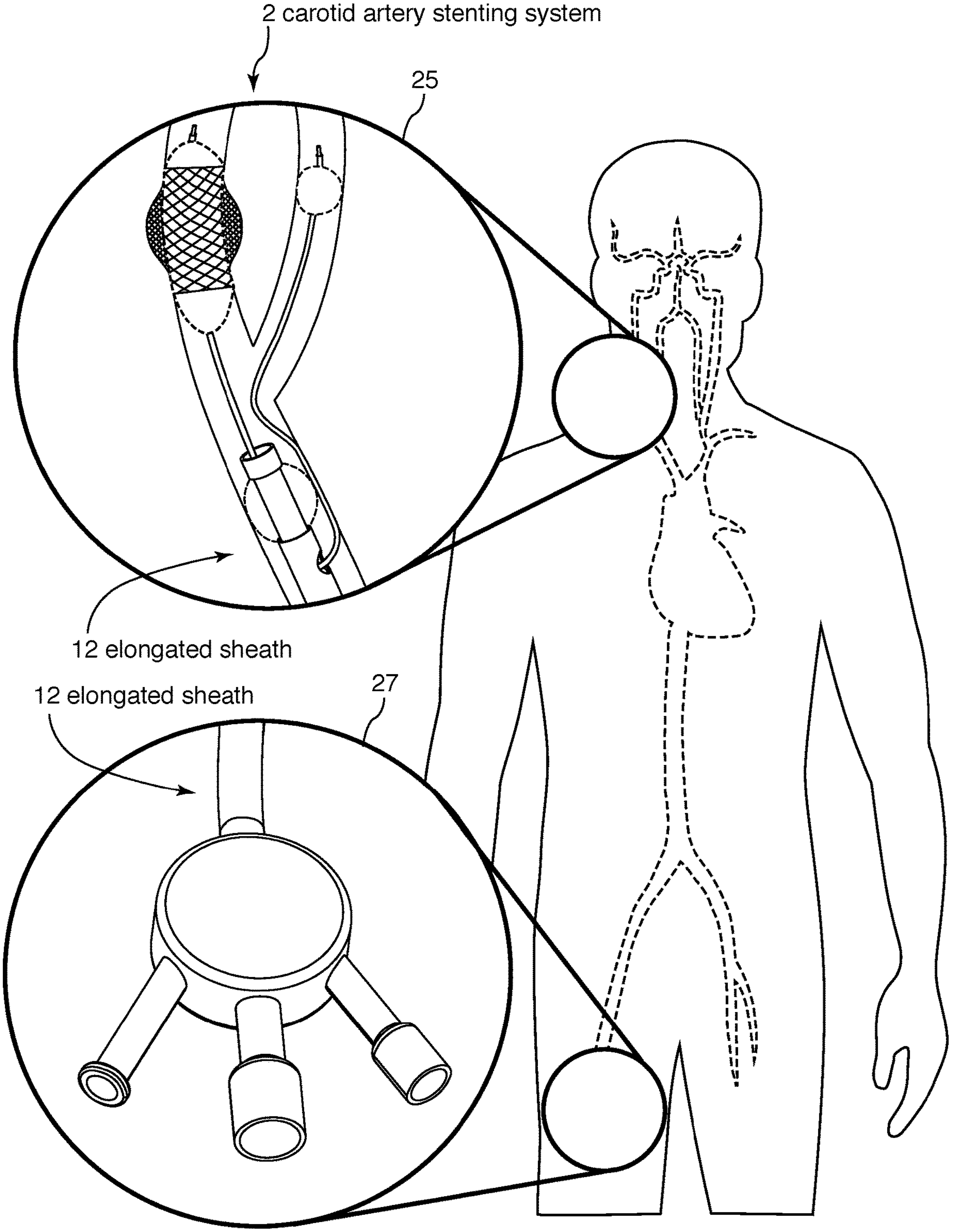
FIG. 1 illustrates a diagrammatic view of a person undergoing a carotid artery stenting procedure, according to some embodiments.

2—Carotid artery stenting system
4—Stent
5—Plaque
6—Lumen
8—Interior
8*a*—Interior
11—Catheter
12—Sheath
14*a*—Access port
14*b*—Access port
15—Lumen
16*a*—Inflation port
17—Catheter
18*a*—Inflatable balloon
18*b*—Inflatable balloon
18*c*—Inflatable balloon
20*a*—Distal port
20*b*—Distal port
22—Lumen
26—Arrow
30—Lumen
33—Opening
35—Opening
37—Diameter
49—Common carotid artery
50—Internal carotid artery
51—External carotid artery
59*a*—Distal end
60*a*—Central axis
75—Portion
90—Proximal portion
93—Distal portion
94—Distal portion FIG. 1 illustrates a diagrammatic view of a person undergoing a carotid artery stenting procedure. As indicated by enlarged circle area 27, an elongated sheath 12 can be inserted into an artery (e.g., a femoral artery). A proximal portion of the elongated sheath 12 can remain outside of the patient's body while a distal portion of the elongated sheath 12 is advanced toward another artery (e.g., a common carotid artery 49) as indicated by enlarged circle area 25.

Figure 2:
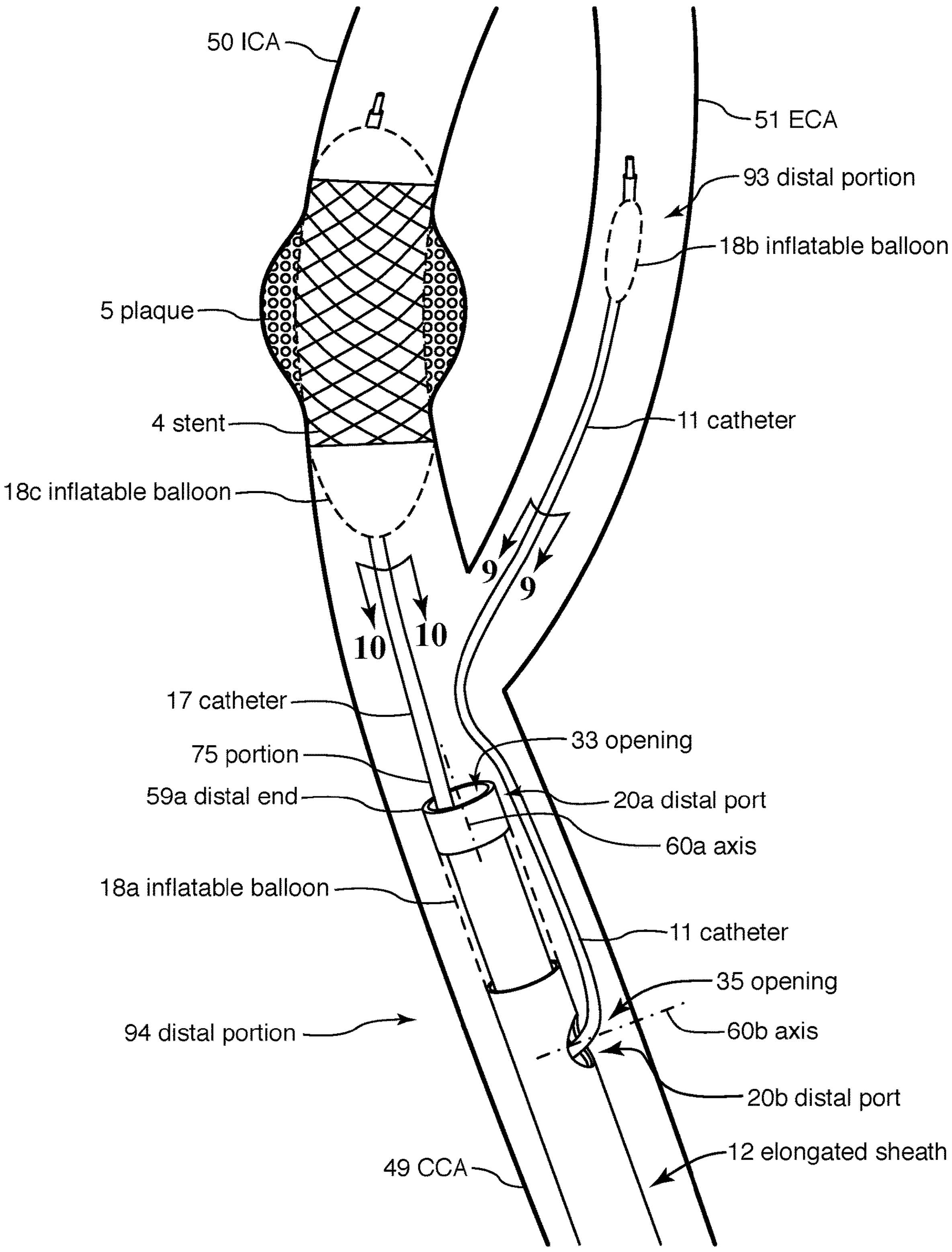
FIGS. 2-4 illustrate perspective views of distal portions of a carotid artery stenting system, according to some embodiments.

FIG. 2 illustrates a perspective view of a common carotid artery 49, an internal carotid artery 50, and an external carotid artery 51. A distal portion 94 of an elongated sheath 12 can be located in the common carotid artery 49. The elongated sheath 12 can have a first inflatable balloon 18*a* configured to occlude an area between an outer perimeter of the elongated sheath 12 and an interior of the common carotid artery 49.

Figure 3:
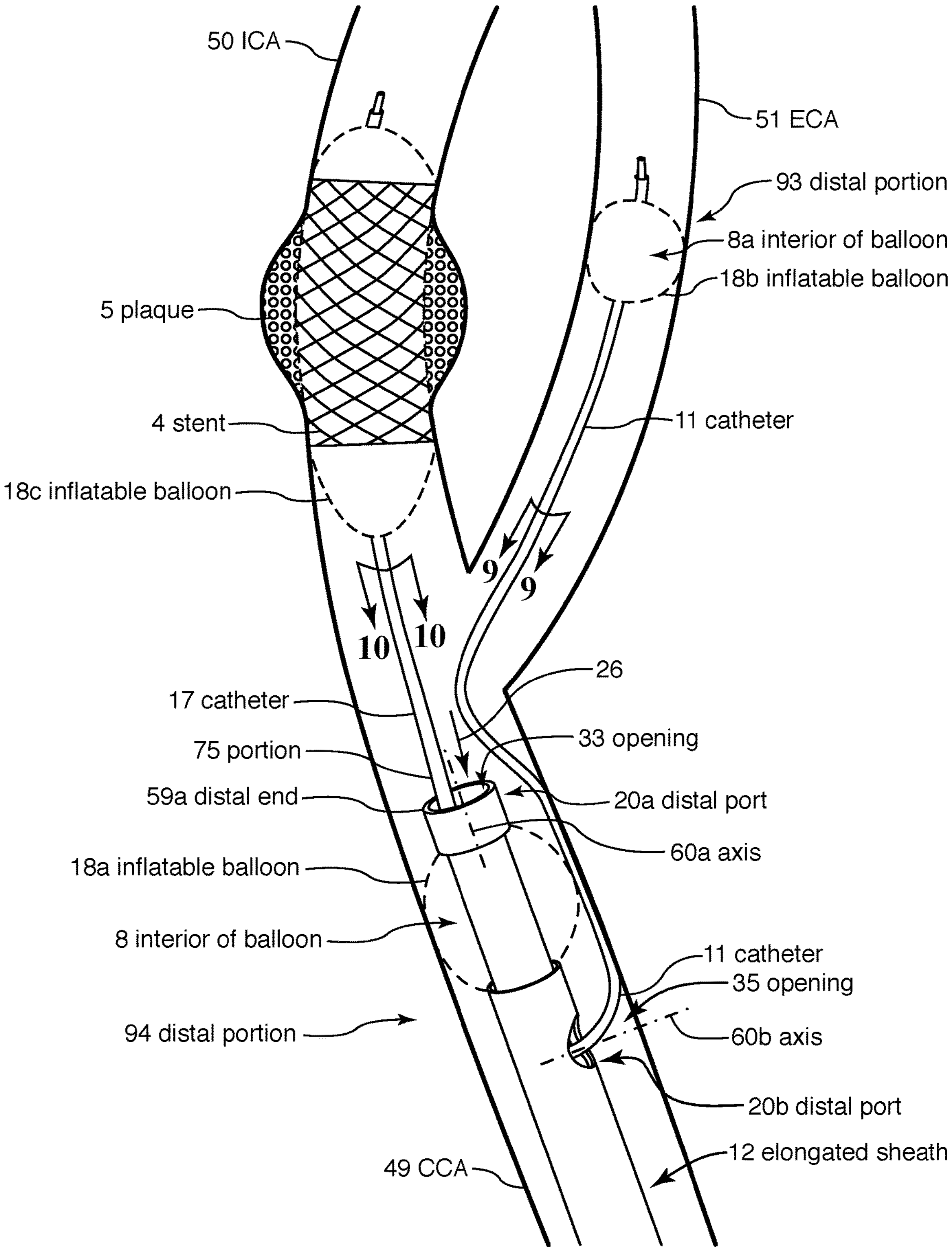

In FIG. 2, the first inflatable balloon 18*a* is in a deflated state and a second inflatable balloon 18*b* is in a deflated state. In FIG. 3, the first inflatable balloon 18*a* is in an inflated state (to at least partially occlude the common carotid artery 49) and the second inflatable balloon 18*b* is in an inflated state (to at least partially occlude the external carotid artery 51, or in some cases to at least partially occlude the internal carotid artery 50).

In some embodiments, in the inflated state of the first inflatable balloon 18*a*, blood can flow into and through an interior of the elongated sheath 12 (as indicated by arrow 26 in FIG. 3). This direction of blood flow is opposite of the "normal" direction of blood flow and can be achieved by fluidly coupling (e.g., using a tube) the common carotid artery 49 with a lower pressure (such as the pressure of a vein).

A distal portion of a first catheter 11 can have a second inflatable balloon 18*b* configured to occlude the external carotid artery 51 or the internal carotid artery 50. The first catheter 11 can comprise a fourth lumen 15 configured to enable inflating the second inflatable balloon 18*b*. The fourth lumen 15 can be fluidly coupled with an interior 8*a* of the second inflatable balloon 18*b*. Pushing liquid (or gas) into a proximal portion of the fourth lumen 15 can cause the second inflatable balloon 18*b* to inflate.

A carotid artery stenting system 2 can comprise a second catheter 17 configured to deliver the stent 4 (e.g., such that the stent 4 pushes plaque 5 radially outward to improve blood flow through the internal carotid artery 50 or the external carotid artery 51). As illustrated in FIG. 3, the second catheter 17 is delivering a stent 4 in the internal carotid artery 50 while the first catheter 11 occludes the external carotid artery 51, but in some embodiments, the second catheter 17 delivers a stent 4 in the external carotid artery 51 while the first catheter 11 occludes the internal carotid artery 50.

Human anatomy varies greatly. The idealized anatomy illustrated in FIG. 3 is just one of many possible anatomies. A carotid artery stenting system size that works well for one patient might be extremely challenging or even completely impractical in another patient. Delivering previous carotid artery stenting systems is very challenging, especially in patients who are older and have complex anatomies. Some embodiments enable customizing not only the distance between the elongated sheath 12 and the stent 4, but also enable customizing the distance between the first inflatable balloon 18 *a* and the second inflatable balloon 18 *b*. Customizing both of these distances enables physicians to easily optimize the carotid artery stenting system 2 for each patient's unique anatomy during the carotid artery stenting.

Figure 4:
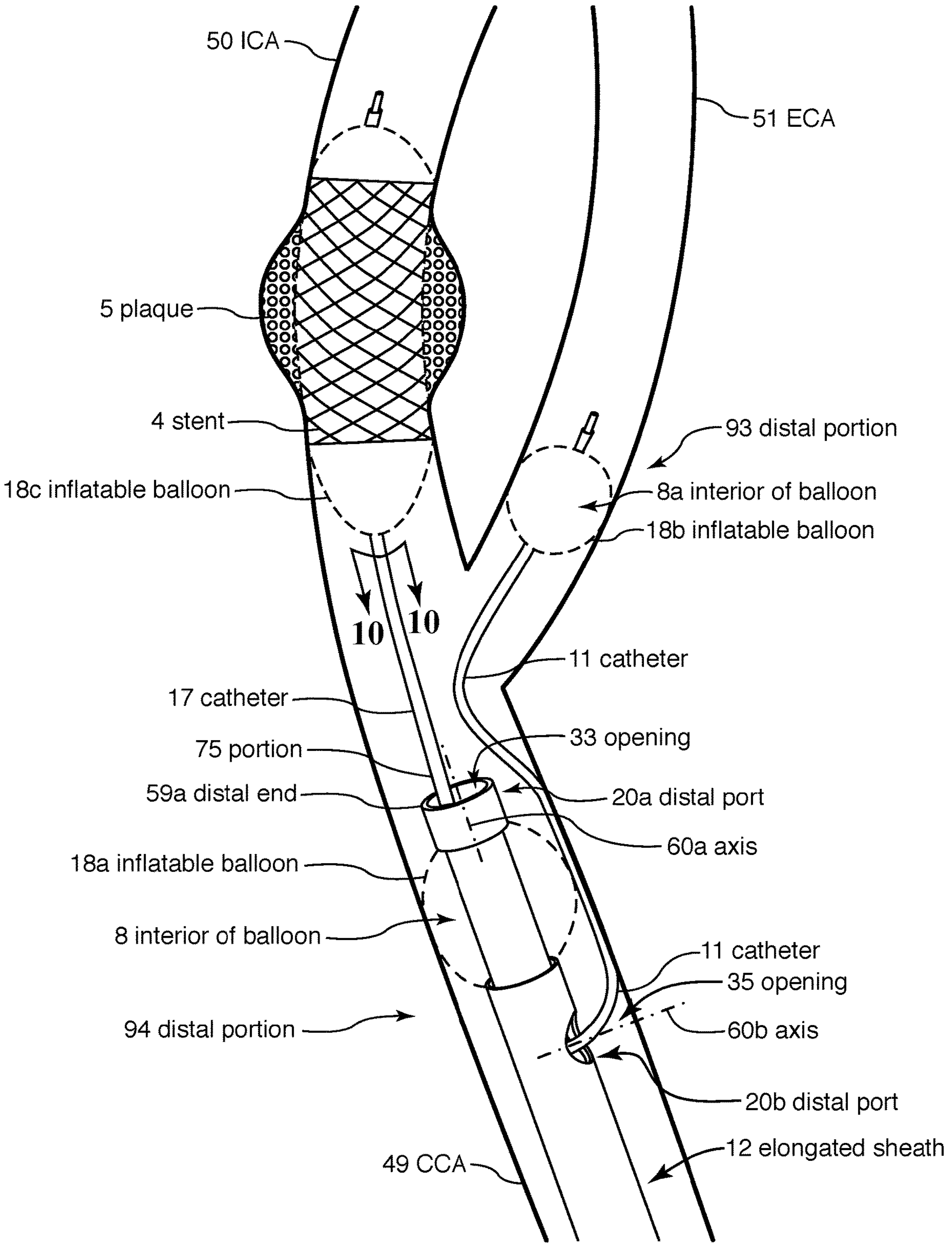

FIG. 3 illustrates a first distance between the first inflatable balloon 18*a* and the second inflatable balloon 18*b*. FIG. 4 illustrates a second distance (that is shorter than the first distance) between the first inflatable balloon 18*a* and the second inflatable balloon 18*b*.

Figure 5:
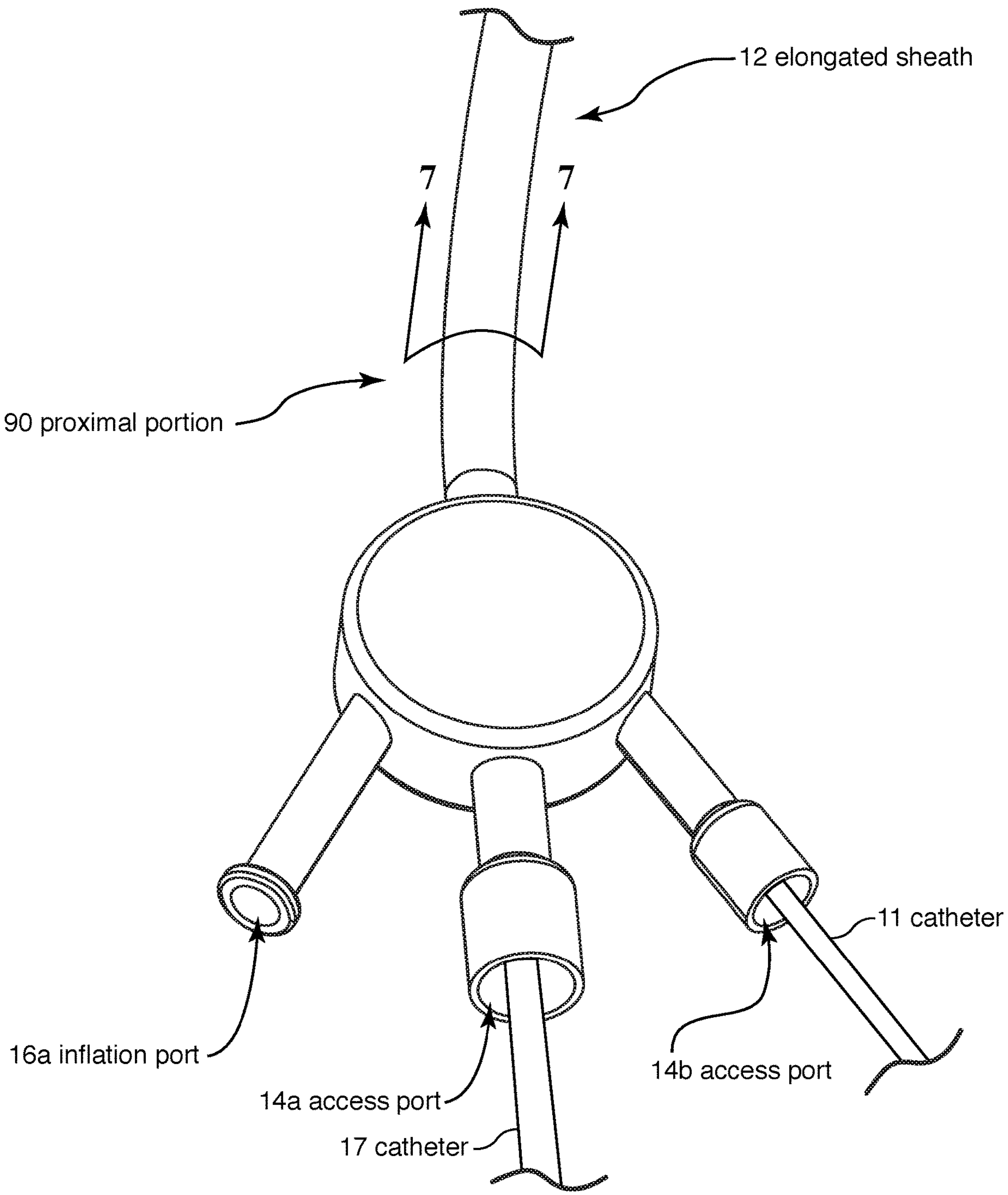
FIG. 5 illustrates a perspective view of a proximal portion of a carotid artery stenting system, according to some embodiments.

FIG. 5 illustrates a proximal portion of the carotid artery stenting system 2. The proximal portion 90 of the elongated sheath 12 can be long enough to reach from a femoral artery access site to at least one of an internal carotid artery 50, an external carotid artery 51, and a common carotid artery 49 of the patient. The proximal portion 90 can be directly coupled to the most proximal portion of the elongated sheath 12 that is shown in FIG. 3.

Figure 7:
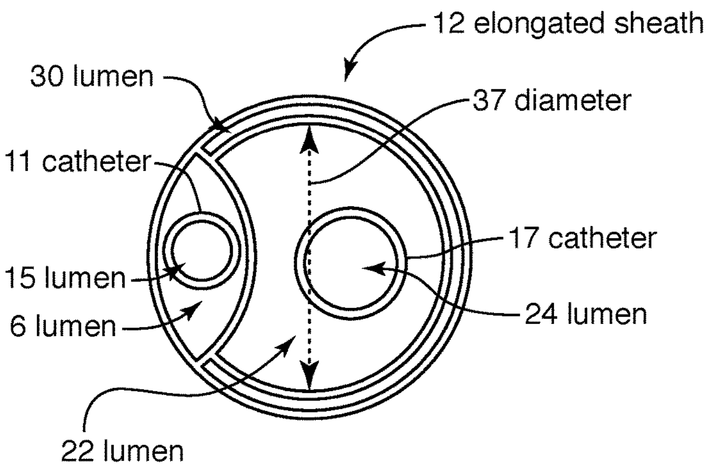

FIG. 7 illustrates a cross-sectional view taken along line 7-7 in FIG. 5. FIG. 7 illustrates a portion of the first catheter 11 in a lumen 6 of the elongated sheath 12. FIG. 7 illustrates a portion of the second catheter 17 in a lumen 22 of the elongated sheath 12. Another lumen 30 of the elongated sheath 12 can be used to inflate the first inflatable balloon 18*a*. Many different cross-sectional shapes can be used with the elongated sheath 12.

Figure 6:
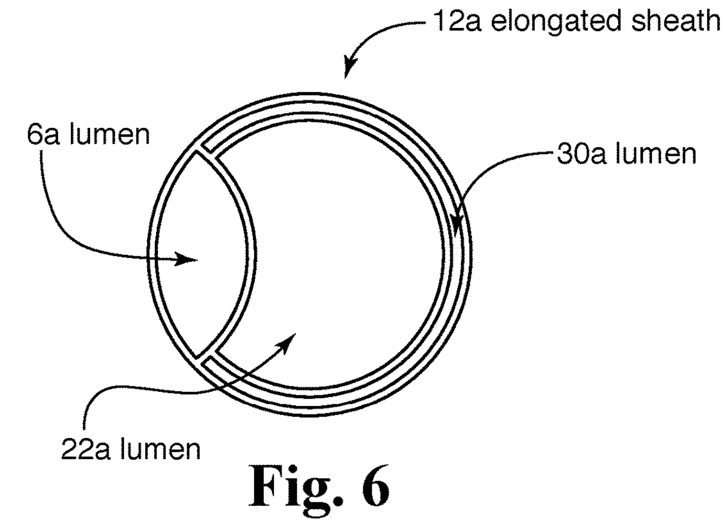
FIGS. 6-8 illustrate cross-sectional views of sheaths, according to some embodiments.
Figure 8:
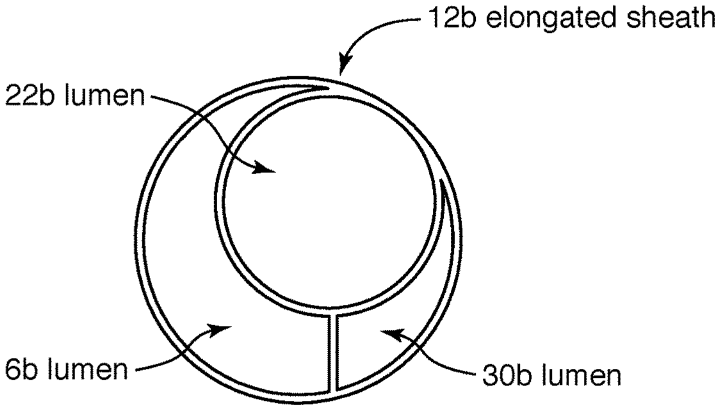

FIGS. 6 and 8 illustrate alternative cross sections of the elongated sheath 12. FIG. 6 illustrates a cross section of an elongated sheath 12*a* that can have any of the features of elongated sheath 12. The elongated sheath 12*a* has lumens 6*a*, 30*a*, 22*a*. The sizes of the lumens 6*a*, 30*a*, 22*a* can be increased and decreased. For example, in some embodiments, lumen 6*a* is increased in size to accommodate a larger balloon catheter.

FIG. 8 illustrates a cross section of an elongated sheath 12*b* that can have any of the features of elongated sheath 12. The elongated sheath 12*b* has lumens 6*b*, 30*b*, 22*b*. The sizes of the lumens 6*b*, 30*b*, 22*b* can be increased and decreased.

Figure 9:
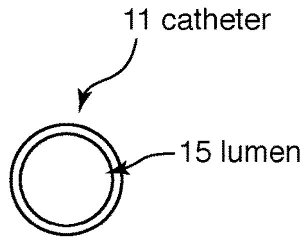
FIGS. 9 and 10 illustrate cross-sectional views of catheters, according to some embodiments.

FIG. 9 illustrates a cross-sectional view of the first catheter 11 taken along line 9-9 in FIG. 3. The first catheter 11 can comprise a lumen 15 configured to inflate a balloon 18*b*. The lumen 15 can be fluidly coupled with an interior 8*a* of the balloon 18*b*.

Figure 10:
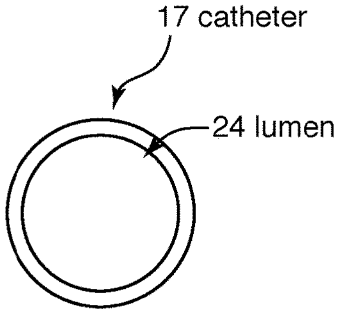

FIG. 10 illustrates a cross-sectional view of the second catheter 17 taken along line 10-10 10 in FIG. 3. The second catheter 17 can comprise a lumen 24 configured to inflate a balloon 18*c*. The lumen 24 can be fluidly coupled with an interior of the balloon 18*c* (to enable inflating the balloon 18*c*).

A carotid artery stenting system 2 can comprise an elongated sheath 12 configured for insertion into an artery. In some embodiments, an elongated sheath 12 comprises a distal portion 94 having a first inflatable balloon 18*a* and a first distal port 20*a* configured to enable a stent 4 to exit the elongated sheath 12; a proximal portion 90 having a first inflation port 16*a* and a first access port 14*a*; a first lumen 22 extending between the first access port 14*a* and the first distal port 20*a*; and/or a second lumen 30 extending between the first inflation port 16*a* and a first interior 8 of the first inflatable balloon 18*a*.

A distal portion 94 of the elongated sheath 12 can comprise a second distal port 20*b*. The proximal portion 90 of the elongated sheath 12 can comprise a second access port 14*b*. The elongated sheath 12 can comprise a third lumen 6 extending between the second distal port 20*b* and the second access port 14*b*. A carotid artery stenting system 2 can comprise a first catheter 11 having a second inflatable balloon 18*b* and a fourth lumen 15 configured to enable inflating the second inflatable balloon 18*b*.

At least a portion of the first catheter 11 can be located in the third lumen 6 of the elongated sheath 12 such that a distance between the first inflatable balloon 18*a* and the second inflatable balloon 18*b* can be customized by moving the portion of the first catheter 11 at least one of distally and proximally inside the third lumen 6 of the elongated sheath 12.

FIG. 7 illustrates a portion of the first catheter 11 located in the third lumen 6 of the elongated sheath 12. A distance between the first inflatable balloon 18*a* and the second inflatable balloon 18*b* can be customized by moving the portion of the first catheter 11 at least one of distally and proximally inside the third lumen 6 of the elongated sheath 12. FIG. 5 illustrates an exposed portion of the catheter 11 that is located proximally relative to an access port 14*b*. The exposed portion is located outside of the access port 14*b* such that the physician can secure the exposed portion between her fingers, and then can push the exposed portion distally (into the access port 14*b*) to increase the distance between the first inflatable balloon 18*a* and the second inflatable balloon 18*b*. The physician can pull the exposed portion proximally (away from the access port 14*b*) to pull more of the catheter 11 out of the elongated sheath 12 and to decrease the distance between the first inflatable balloon 18*a* and the second inflatable balloon 18*b*.

A carotid artery stenting system 2 can comprise a second catheter 17 configured to deliver the stent 4. At least a first portion of the second catheter 17 can be located in the first lumen 22 of the elongated sheath 12. A second portion of the second catheter 17 can be located in the first distal port 20*a*.

The second catheter 17 can comprise a distal portion having a third inflatable balloon 18*c* configured to expand the stent 4 in at least one of an internal carotid artery 50, an external carotid artery 51, a common carotid artery 49, any artery in a body of a patient, and any vein in a body of a patient.

The physician can also customize a distance between the first inflatable balloon 18*a* and the third inflatable balloon 18*c*. FIG. 7 illustrates a portion of a second catheter 17 located in a lumen 22 of the elongated sheath 12.

FIG. 5 illustrates an exposed portion of the second catheter 17 that is located proximally relative to an access port 14*a*. The exposed portion is located outside of the access port 14*a* such that the physician can secure the exposed portion between her fingers, and then can push the exposed portion distally (into the access port 14*a*) to increase the distance between the first inflatable balloon 18*a* and the third inflatable balloon 18*c*. The physician can pull the exposed portion proximally (away from the access port 14*a*) to pull more of the second catheter 17 out of the elongated sheath 12 and to decrease the distance between the first inflatable balloon 18*a* and the third inflatable balloon 18*c*.

The first inflatable balloon 18*a* can be in a first inflated occlusion state in a common carotid artery 49, and the second inflatable balloon 18*b* can be in a second inflated occlusion state in an external carotid artery 51.

A carotid artery stenting system 2 can comprise a second catheter 17 configured to deliver the stent 4. At least a first portion of the second catheter 17 can be located in the first lumen 22 of the elongated sheath 12. A second portion of the second catheter 17 can be located in the first distal port 20*a*. The stent 4 and a distal portion of the second catheter 17 can be located in an internal carotid artery 50.

The first inflatable balloon 18*a* can be in a first inflated occlusion state in a common carotid artery 49. The second inflatable balloon 18*b* can be in a second inflated occlusion state in an internal carotid artery 50.

A carotid artery stenting system 2 can comprise a second catheter 17 configured to deliver the stent 4. At least a first portion of the second catheter 17 can be located in the first lumen 22 of the elongated sheath 12. A second portion of the second catheter 17 can be located in the first distal port 20*a*. The stent 4 and a distal portion of the second catheter 17 can be located in an external carotid artery 51.

A carotid artery stenting system 2 can comprise a second catheter 17 configured to deliver the stent 4. At least a first portion of the second catheter 17 can be located in the first lumen 22 of the elongated sheath 12. A first opening 33 of the first distal port 20*a* can be oriented within plus or minus ten degrees (and/or within plus or minus twenty degrees) of a central axis 60*a* of a distal end 59*a* of the elongated sheath 12 such that the first distal port 20*a* is configured to enable a second portion 75 of the second catheter 17 that is located distally relative to the distal end 59*a* of the elongated sheath 12 to be axially aligned with the central axis 60*a*.

Some embodiments comprise a second opening 35 of the second distal port 20*b*. The second opening 35 can be oriented at an angle of at least twenty degrees (and/or at least forty degrees) relative to the central axis 60*a*.

The second opening 35 can comprise a central axis 60*b* that is oriented within plus or minus twenty degrees of perpendicular relative to the central axis 60*a* of the distal end 59*a* of the elongated sheath 12.

In some embodiments, the second opening 35 is located on the distal end 59*a* of the elongated sheath 12 rather than being located on a radially outward facing side of the elongated sheath 12. The distal end 59*a* of the elongated sheath 12 can comprise the second opening 35 of the second distal port 20*b*. The second opening 35 can be oriented at an angle of less than twenty degrees relative to the central axis 60*a*. The second opening 35 can be located distally or proximally relative to the first inflatable balloon 18*a*.

The first inflatable balloon 18*a* can be located on a first outer perimeter of the elongated sheath 12. In some embodiments, the second inflatable balloon 18*b* is not located on a second outer perimeter of the elongated sheath 12. The second inflatable balloon 18*b* can be located on a third outer perimeter of the first catheter 11. The first catheter 11 can comprise a first distal portion 93 having the second inflatable balloon 18*b*. The first distal portion 93 of first catheter 11 can be configured to move distally and rotationally independent of the first inflatable balloon 18*a*.

While the first inflatable balloon 18*a* is held in place in the common carotid artery 49 (by friction or by holding a proximal portion 90 of the sheath 12), the physician can move the distal portion 93 (shown in FIG. 2) of the first catheter 11 independently of the first inflatable balloon 18*a* by pushing an exposed portion of the first catheter 11 (shown in FIG. 5) distally into the access port 14*b*. The physician can pull the exposed portion of the first catheter 11 to move the second inflatable balloon 18*b* independently of the first inflatable balloon 18*a*.

The physician can pull the exposed portion of the first catheter 11 proximally (away from the access port 14*b*) to pull more of the catheter 11 out of the elongated sheath 12 and to decrease a distance between the first inflatable balloon 18*a* and the first distal portion 93 of first catheter 11.

The physician can rotate the exposed portion of the first catheter 11 (while holding the proximal portion 90 of the elongated sheath 12 to prevent the proximal portion 90 from rotating) to rotate the first distal portion 93 (and the second inflatable balloon 18*b*) of first catheter 11 independently of the first inflatable balloon 18*a*.

As shown in FIG. 7, the second lumen 30 and the third lumen 6 are located radially outward relative to the first lumen 22. The first lumen 22 can comprise a first cross-sectional area that is at least three times larger than a second cross-sectional area of the second lumen 30. The first cross-sectional area can be at least two times larger than a third cross-sectional area of the third lumen 6.

In some embodiments, an inner diameter 37 of the first lumen 22 of the elongated sheath 12 is less than seven French. An inner diameter 37 of the first lumen 22 of the elongated sheath 12 can be less than six French. An inner diameter 37 of the first lumen 22 of the elongated sheath 12 can be less than four French.

The elongated sheath 12 can comprise any length. The elongated sheath 12 can comprise a working length configured to enable a distal end 59*a* of the elongated sheath 12 to reach an internal carotid artery 50 of a person from a femoral artery arteriotomy.

Some carotid artery stenting embodiments comprise obtaining an elongated sheath 12 having a distal portion 94 and a proximal portion 90. The distal portion 94 of the elongated sheath 12 can comprise a first inflatable balloon 18*a* and a first distal port 20*a* configured to enable a stent 4 to exit the elongated sheath 12. The proximal portion 90 of the elongated sheath 12 can comprise a first inflation port 16*a* and a first access port 14*a*. The elongated sheath 12 can comprise a first lumen 22 and a second lumen 30. The first lumen 22 can extend between the first access port 14*a* and the first distal port 20*a* such that the first lumen 22 fluidly couples the first access port 14*a* and the first distal port 20*a*.

The second lumen 30 can extend between the first inflation port 16*a* and a first interior 8 of the first inflatable balloon 18*a* such that the second lumen 30 fluidly couples the first inflation port 16*a* and the first interior 8 of the first inflatable balloon 18*a*.

The distal portion 94 of the elongated sheath 12 can comprise a second distal port 20*b*. The proximal portion 90 of the elongated sheath 12 can comprise a second access port 14*b*. The elongated sheath 12 can comprise a third lumen 6 extending between the second distal port 20*b* and the second access port 14*b* such that the third lumen 6 fluidly couples the second distal port 20*b* and the second access port 14*b*.

Some embodiments comprise inserting the elongated sheath 12 into an artery to perform a medical procedure. Many different types of medical procedures in many different parts of a patient's body can be performed with embodiments described herein and/or incorporated by reference.

Some embodiments comprise moving a first catheter 11 distally (and/or proximally) in the third lumen 6 of the elongated sheath 12. The first catheter 11 can comprise a second inflatable balloon 18*b* and a fourth lumen 15 configured to enable inflating the second inflatable balloon 18*b*.

Some embodiments comprise inflating the first inflatable balloon 18*a* in a common carotid artery 49 to at least partially occlude the common carotid artery 49; customizing a distance between the first inflatable balloon 18*a* in the common carotid artery 49 and the second inflatable balloon 18*b* in an external carotid artery 51 (or in an internal carotid artery 50) by moving a portion of the first catheter 11 at least one of distally and proximally inside the third lumen 6 of the elongated sheath 12; and/or inflating the second inflatable balloon 18*b* in the external carotid artery 51 (or in the internal carotid artery 50) to at least partially occlude the external carotid artery 51 (or to at least partially occlude the internal carotid artery 50).

Some embodiments comprise moving a second catheter 17 having the stent 4 distally in the first lumen 22 of the elongated sheath 12 to move the stent 4 distally through at least a portion of the first lumen 22 and then into an internal carotid artery 50 (or into an external carotid artery 51).

Some embodiments comprise delivering the stent 4 to a location in the internal carotid artery 50 while a distal end 59*a* of the elongated sheath 12 is positioned in the common carotid artery 49; while occluding an area between an outer perimeter of the elongated sheath 12 and an inner wall of the common carotid artery 49 with the first inflatable balloon 18*a*; while occluding the external carotid artery 51 with the second inflatable balloon 18*b* of the first catheter 11; and/or while fluidly coupling the common carotid artery 49 to a pressure source having a lower pressure than a blood pressure of the common carotid artery 49 to apply a suction force to blood in the common carotid artery 49. The pressure source can comprise a vein.

Some embodiments comprise delivering the stent 4 to a location in the external carotid artery 51 while a distal end 59*a* of the elongated sheath 12 is positioned in the common carotid artery 49; while occluding an area between an outer perimeter of the elongated sheath 12 and an inner wall of the common carotid artery 49 with the first inflatable balloon 18*a*; while occluding the internal carotid artery 50 with the second inflatable balloon 18*b* of the first catheter 11; and/or while fluidly coupling the common carotid artery 49 to a pressure source having a lower pressure than a blood pressure of the common carotid artery 49 to apply a suction force to blood in the common carotid artery 49. The pressure source can comprise a vein.

Some embodiments comprise using a tube to fluidly couple the common carotid artery 49 to the vein. Some embodiments comprise reversing a flow direction of the blood to suction emboli from at least one of the internal carotid artery 50, the external carotid artery 51, and the common carotid artery 49.

Interpretation

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

To increase the clarity of various features, other features are not labeled in each figure.

The various features and processes described above may be used independently of one another, or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments can include A, B, and C. The term "and/or" is used to avoid unnecessary redundancy.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

What is claimed is:

1. A carotid artery stenting system comprising:

an elongated sheath configured for insertion into an artery, the elongated sheath comprising:
- a distal portion having:
  - a first inflatable balloon located on a first outer perimeter of the elongated sheath;
  - a first distal port configured to enable a stent to exit the elongated sheath; and
  - a second distal port located on a second outer perimeter of the elongated sheath and proximal to the first distal port and the first inflatable balloon, wherein the second distal port is configured to enable a first catheter to exit the elongated sheath;
- a proximal portion having a first inflation port, a first access port, and a second access port;
- a first lumen extending between the first access port and the first distal port; and
- a second lumen extending between the first inflation port and a first interior of the first inflatable balloon; and
- a third lumen extending between the second distal port and the second access port.

2. The carotid artery stenting system of claim 1, further comprising the first catheter having a second inflatable balloon and a fourth lumen configured to enable inflating the second inflatable balloon.

3. The carotid artery stenting system of claim 2, wherein at least a portion of the first catheter is located in the third lumen of the elongated sheath such that a distance between the first inflatable balloon and the second inflatable balloon can be customized by moving the portion of the first catheter at least one of distally or proximally inside the third lumen of the elongated sheath.

4. The carotid artery stenting system of claim 3, further comprising a second catheter configured to deliver the stent, wherein at least a first portion of the second catheter is located in the first lumen of the elongated sheath, and a second portion of the second catheter is located in the first distal port.

5. The carotid artery stenting system of claim 4, wherein the second catheter comprises a distal portion having a third inflatable balloon configured to expand the stent in at least one of an internal carotid artery, an external carotid artery, or a common carotid artery.

6. The carotid artery stenting system of claim 3, further comprising a second catheter configured to deliver the stent, wherein at least a first portion of the second catheter is located in the first lumen of the elongated sheath, and a first opening of the first distal port is oriented within plus or minus ten degrees of a central axis of a distal end of the elongated sheath such that the first distal port is configured to enable a second portion of the second catheter that is located distally relative to the distal end of the elongated sheath to be axially aligned with the central axis.

7. The carotid artery stenting system of claim 6, further comprising a second opening of the second distal port, wherein the second opening is oriented at an angle of at least twenty degrees relative to the central axis.

8. The carotid artery stenting system of claim 6, further comprising a second opening of the second distal port, wherein the second opening is oriented at an angle of at least forty degrees relative to the central axis.

9. The carotid artery stenting system of claim 6, further comprising a second opening of the second distal port, wherein the second opening is oriented at an angle of less than twenty degrees relative to the central axis.

10. The carotid artery stenting system of claim 3, wherein the second inflatable balloon is not located on the second outer perimeter of the elongated sheath, and the second inflatable balloon is located on a third outer perimeter of the first catheter, wherein the first catheter comprises a first distal portion having the second inflatable balloon, and the first distal portion of first catheter is configured to move distally and rotationally independent of the first inflatable balloon.

11. The carotid artery stenting system of claim 3, wherein the second lumen and the third lumen are located radially outward relative to the first lumen.

12. The carotid artery stenting system of claim 3, wherein the first lumen comprises a first cross-sectional area that is at least three times larger than a second cross-sectional area of the second lumen.

13. The carotid artery stenting system of claim 12, wherein the first cross-sectional area is at least two times larger than a third cross-sectional area of the third lumen.

14. The carotid artery stenting system of claim 3, wherein a diameter of the first lumen of the elongated sheath is less than at least one of seven French or six French.

15. The carotid artery stenting system of claim 3, wherein the elongated sheath comprises a working length configured to enable a distal end of the elongated sheath to reach an internal carotid artery of a person from a femoral artery arteriotomy.

16. The carotid artery stenting system of claim 1, wherein the first outer perimeter of the elongated sheath is continuous with the second outer perimeter of the elongated sheath.

17. A carotid artery stenting method comprising:

obtaining an elongated sheath having a distal portion and a proximal portion; and inserting the elongated sheath into an artery, wherein the distal portion of the elongated sheath comprises:

a first inflatable balloon located on a first outer perimeter of the elongated sheath;

a first distal port configured to enable a stent to exit the elongated sheath; and a second distal port located on a second outer perimeter of the elongated sheath and proximal to the first distal port and the first inflatable balloon, wherein the second distal port is configured to enable a first catheter to exit the elongated sheath, wherein the proximal portion of the elongated sheath comprises a first inflation port and a first access port, wherein the elongated sheath further comprises a first lumen and a second lumen, wherein the first lumen extends between the first access port and the first distal port, wherein the second lumen extends between the first inflation port and a first interior of the first inflatable balloon, wherein the proximal portion of the elongated sheath comprises a second access port proximal to the first distal port and the first inflatable balloon, and wherein the elongated sheath further comprises a third lumen extending between the second distal port and the second access port.

18. The carotid artery stenting method of claim 17, further comprising moving the first catheter distally in the third lumen of the elongated sheath, wherein the first catheter comprises a second inflatable balloon and a fourth lumen configured to enable inflating the second inflatable balloon.

19. The carotid artery stenting method of claim 18, further comprising:

inflating the first inflatable balloon in a common carotid artery to at least partially occlude the common carotid artery;

customizing a distance between the first inflatable balloon in the common carotid artery and the second inflatable balloon in an external carotid artery by moving a portion of the first catheter at least one of distally or proximally inside the third lumen of the elongated sheath; and inflating the second inflatable balloon in the external carotid artery to at least partially occlude the external carotid artery.

20. The carotid artery stenting method of claim 19, further comprising moving a second catheter having the stent distally in the first lumen of the elongated sheath to move the stent distally through at least a portion of the first lumen and then into an internal carotid artery.

21. The carotid artery stenting method of claim 20, further comprising:

delivering the stent to a location in the internal carotid artery while a distal end of the elongated sheath is positioned in the common carotid artery;

while occluding an area between the second outer perimeter of the elongated sheath and an inner wall of the common carotid artery with the first inflatable balloon;

while occluding the external carotid artery with the second inflatable balloon of the first catheter; and while fluidly coupling the common carotid artery to a pressure source having a lower pressure than a blood pressure of the common carotid artery to apply a suction force to blood in the common carotid artery.

22. The carotid artery stenting method of claim 21, wherein the pressure source comprises a vein, the method further comprising using a tube to fluidly couple the common carotid artery to the vein.

23. The carotid artery stenting method of claim 21, further comprising reversing a flow direction of the blood to suction emboli from at least one of the internal carotid artery, the external carotid artery, or the common carotid artery.

24. The carotid artery stenting method of claim 17, wherein the first outer perimeter of the elongated sheath is continuous with the second outer perimeter of the elongated sheath.

* * * * *